US012789394B2

(12) United States Patent
Liu et al.

(10) Patent No.: US 12,789,394 B2
(45) Date of Patent: Nov. 10, 2026

(54) END-EFFECTOR ATTACHMENTS

(71) Applicant: EDDA TECHNOLOGY, INC., Princeton, NJ (US)

(72) Inventors: Yijun Liu, Bayonne, NJ (US); Yuanfeng Mao, Princeton, NJ (US); Guo-Qing Wei, Plainsboro, NJ (US); Li Fan, Belle Mead, NJ (US); Xiaolan Zeng, Princeton, NJ (US); Jianzhong Qian, Princeton Junction, NJ (US)

(73) Assignee: EDDA TECHNOLOGY, INC., Princeton, NJ (US)

( * ) Notice: Subject to any disclaimer, the term of this patent is extended or adjusted under 35 U.S.C. 154(b) by 0 days.

(21) Appl. No.: 19/057,504

(22) Filed: Feb. 19, 2025

(65) Prior Publication Data

US 2026/0241581 A1 Aug. 20, 2026

(51) Int. Cl.
*B25J 15/04* (2006.01)
*A61B 34/30* (2016.01)

(52) U.S. Cl.
CPC .......... *B25J 15/0408* (2013.01); *A61B 34/30* (2016.02)

(58) Field of Classification Search
CPC .................. B25J 15/0408; A61B 34/30; A61B 2017/00477
See application file for complete search history.

(56) References Cited

U.S. PATENT DOCUMENTS

2020/0016772 A1* 1/2020 Motowaki ............ B25J 15/0408
2023/0404686 A1* 12/2023 Sebring .................. A61B 34/30

* cited by examiner

*Primary Examiner* — Terence Boes
(74) *Attorney, Agent, or Firm* — Venable LLP

(57) ABSTRACT

The present teaching relates to an end-effector attachment that includes a main body and a pivotable portion attached to the main body. The main body includes an end configured to attach to an end-effector. The pivotable portion is configured to pivot between a closed position and an open position. In the closed position, a first surface of the pivotable portion contacts a first surface of the main body and forms a cavity through the end-effector attachment. In the open position, the first surface of the pivotable portion does not contact the first surface of the main body.

17 Claims, 9 Drawing Sheets

END-EFFECTOR ATTACHMENTS

BACKGROUND

1. Technical Field

The present teaching generally relates to robotic end-effectors. More specifically, the present teaching relates to end-effectors having medical device functionalities.

2. Technical Background

Robotic guide systems are routinely used to conduct a wide range of medical procedures, such as surgeries, biopsies, and blood sampling. Such robotic guide systems often include an end-effector, i.e., an articulating arm with an end that can perform various functions, such as gripping needles or other medical instruments. However, prior end-effectors can have shortcomings. For example, switching different instruments can be time-consuming for the physician or guide system operator. And improving the ability to switch between instruments can require end-effector designs that are complicated to design or expensive to maintain.

Thus, there is a need for a solution that addresses these challenges.

SUMMARY

The teachings disclosed herein relate to end-effector attachments and methods for using end-effector attachments as described below.

In one example, an end-effector attachment for a robotic guide system comprises a main body that includes an end configured to attach to an end-effector. The end-effector attachments also comprises a pivotable portion attached to the main body. The pivotable portion is configured to pivot between a closed position, in which a first surface of the pivotable portion contacts a first surface of the main body, and an open position, in which the first surface of the pivotable portion does not contact the first surface of the main body. Furthermore, the first surface of the pivotable portion and the first surface of the main body are shaped to provide a cavity through the end-effector attachment.

In a different example, an end-effector attachment for a robotic guide system comprises a main body and a rotatable portion on an outer surface of the main body. The rotatable portion has a first end configured to engage with an end-effector and a second end configured to be actuated by a user. The end-effector attachment also comprises a cavity that extends through the main body. The cavity is configured to hold an instrument guidable by the robotic guide system.

Another example is a method for using an end-effector attachment that comprises providing an end-effector attachment that includes a main body, a rotatable portion on an outer surface of the main body, a mating portion on the main body configured to mate with a mating portion on an end-effector, a pivotable portion attached to the main body, and a flexible portion on the main body. The pivotable portion is configured to pivot between a closed position, in which a first surface of the pivotable portion contacts a first surface of the main body and causes a cavity to be formed in the end-effector attachment, and an open position, in which the first surface of the pivotable portion does not contact the first surface of the main body. In the closed position, the pivotable portion is engaged with the flexible portion such that the pivotable portion cannot pivot to the open position without deflection of the flexible portion. The method also comprises actuating the rotatable portion to cause a first end of the rotatable portion to move away from the main body and a second end of the rotatable portion to move towards the main body. The first end is configured to engage with a cut-out portion of the end-effector and the second end is configured to be actuated by a user. The method further comprises mating the mating portion of the end-effector attachment with the mating portion of the end-effector. The method further comprises actuating the rotatable portion to cause the first end of the rotatable portion to engage with the cut-out portion on the end-effector.

Additional advantages and novel features will be set forth in part in the description which follows, and in part will become apparent to those skilled in the art upon examination of the following and the accompanying drawings or may be learned by production or operation of the examples. The advantages of the present teachings may be realized and attained by practice or use of various aspects of the methodologies, instrumentalities and combinations set forth in the detailed examples discussed below.

BRIEF DESCRIPTION OF THE DRAWINGS

The apparatuses, methods, and/or systems described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to facilitate a thorough understanding of the relevant teachings. However, it should be apparent to those skilled in the art that the present teachings may be practiced without such details. In other instances, well-known methods, procedures, components, and/or systems have been described at a relatively high-level, without detail, in order to avoid unnecessarily obscuring aspects of the present teachings.

Figure 1:
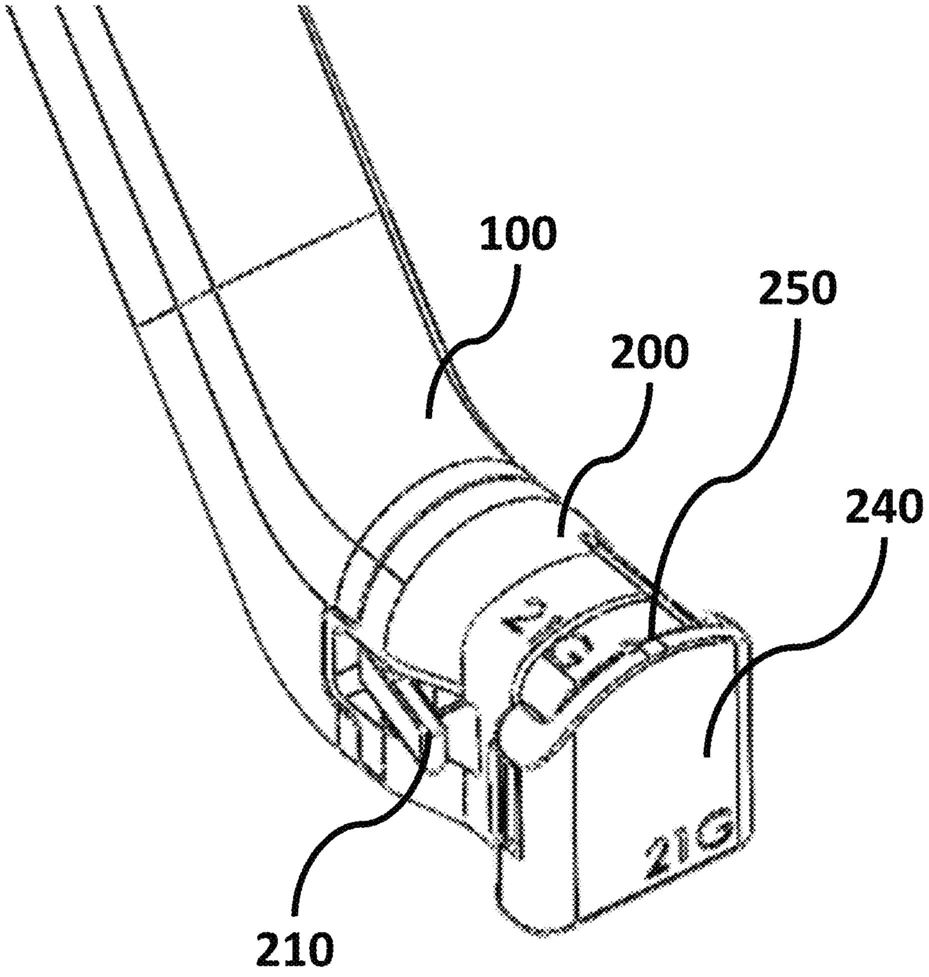
FIG. 1 shows a perspective illustration of an end-effector with an attached exemplary instrument holder as an end-effector attachment.
Figure 2:
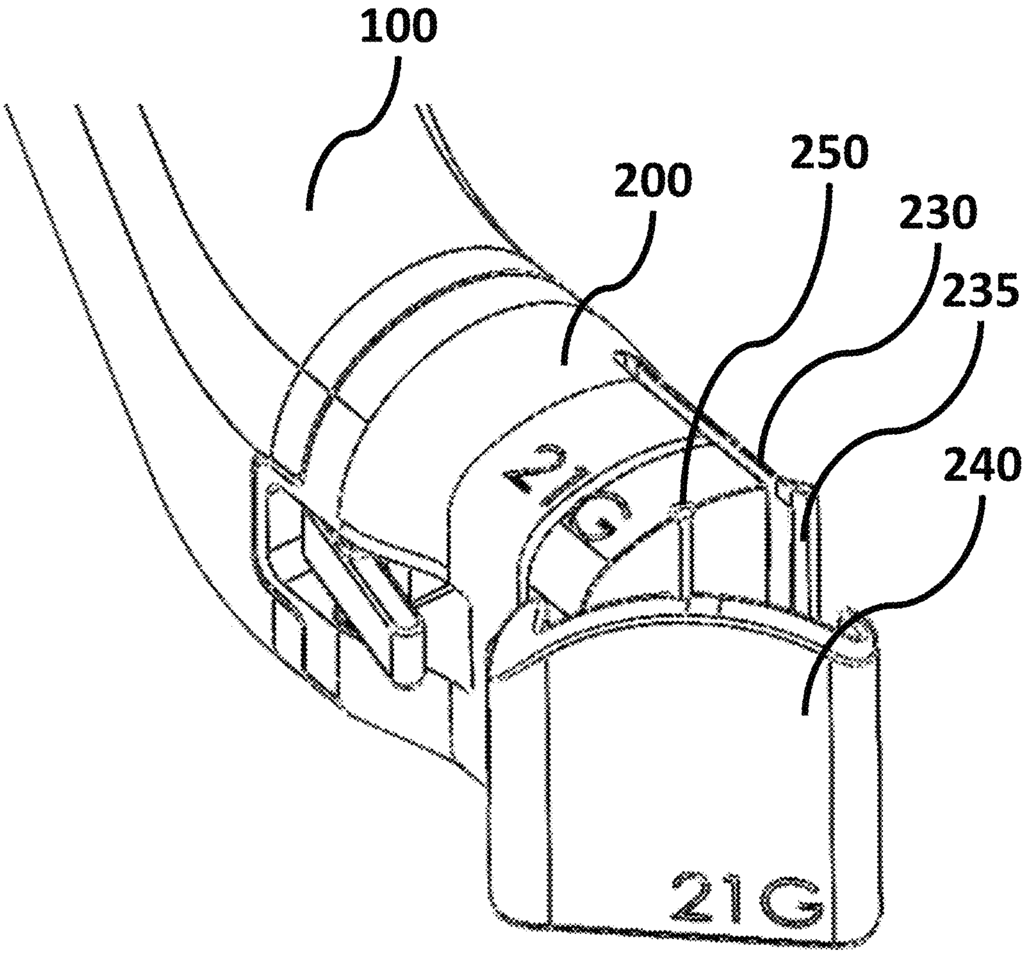
FIG. 2 shows another perspective illustration of an end-effector with an attached exemplary instrument holder.
Figure 3:
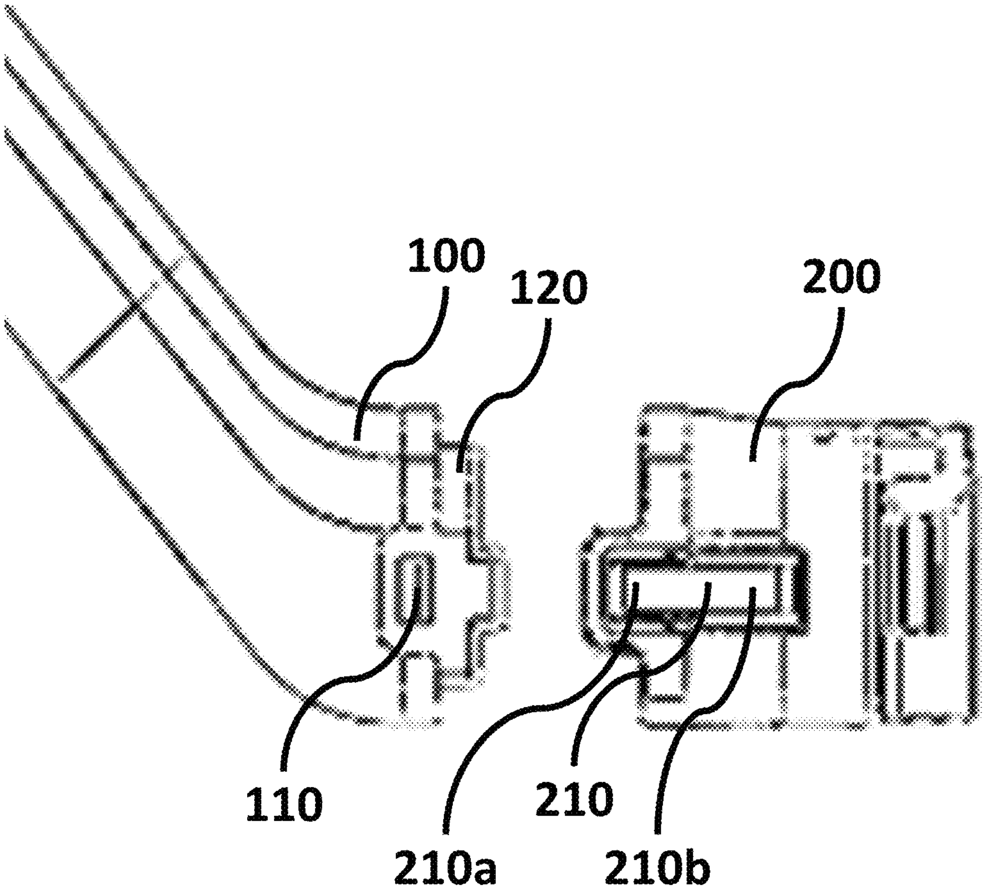
FIG. 3 shows a side illustration of an end-effector with an exemplary end-effector attachment detached from the end-effector.

FIGS. 1-3 show various illustrations of a robotic guide system, in both attached and detached states, according to example embodiments of the invention. FIG. 1 is a perspective illustration of part of the robotic guide system, which includes a robotic end-effector 100 and an end-effector attachment 200 attached to the end-effector 100. As discussed in greater detail below, end-effector attachment 200 is attachable to robotic end-effector 100 via torsional snap fitting 210.

In example embodiments of the invention, end-effector attachment 200 is configured as an instrument holder for instruments such as, for example, needles. In one example embodiment, end-effector attachment 200 includes pivotable door 240, which together with the fixed main body of the end-effector attachment forms an entry point 250 when the pivotable door is closed. Entry point 250 is a cavity within end-effector attachment 200 that, once formed, may be used to securely hold an instrument. In example embodiments of the invention, entry point 200 is a circular cavity for holding a needle. Entry point 250 used in conjunction with a robotic guide system also may provide a predetermined path and angle for penetrating the body of a patient with the instrument.

FIG. 2 is another perspective illustration of part of the robotic guide system. However, in FIG. 2, pivotable door 240 is shown in an open position, rather than a closed position as in FIG. 1. As can be seen from FIG. 2 in conjunction with FIG. 1, pivotable door 240 can be held in the closed position by a bearing surface such as hooked end 235 of flexible plate 230. In particular, deflection of flexible plate 230 can permit the pivotable door 240 to be pivoted into a closed position in which hooked end 235 holds the door, or permit the door to be released from the hooked end and pivoted into an open position. Such deflection of the flexible plate 230 therefore allows for an instrument held within entry point 250 to be released smoothly from the end-effector attachment, unlike prior end-effector attachment which may not release the instrument smoothly, causing injury to a patient.

FIG. 3 is a side illustration of the components of the robotic guide system in which end-effector attachment 200 is detached from end-effector 100. As shown in this figure, torsional snap fitting 210 is engageable with a corresponding structure on end-effector 100, such as cut-out groove 110, in order to attach the end-effector attachment to the end-effector. In an example embodiment, torsional snap fitting 210 includes an outer end 210*a* and an inner end 210*b*. Outer end 210*a* is shaped to mate with groove 110 on end-effector 100. Inner end 210*b* that may be actuated by a user, thereby causing the snap fitting to rotate about its connection to the end-effector attachment, and allowing the outer end 210*a* of torsional snap fitting 210 to engage with (lock) or disengage from (unlock) groove 110.

Figure 4:
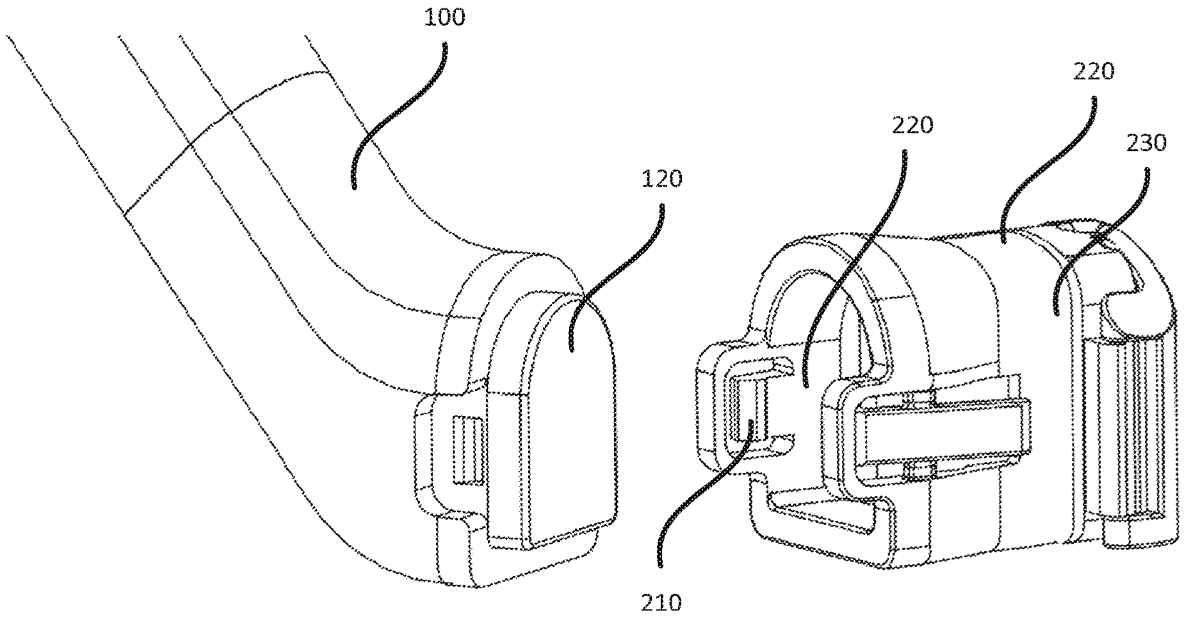
FIG. 4 shows a rendering of an end-effector with an exemplary end-effector attachment detached from the end-effector.
Figure 5:
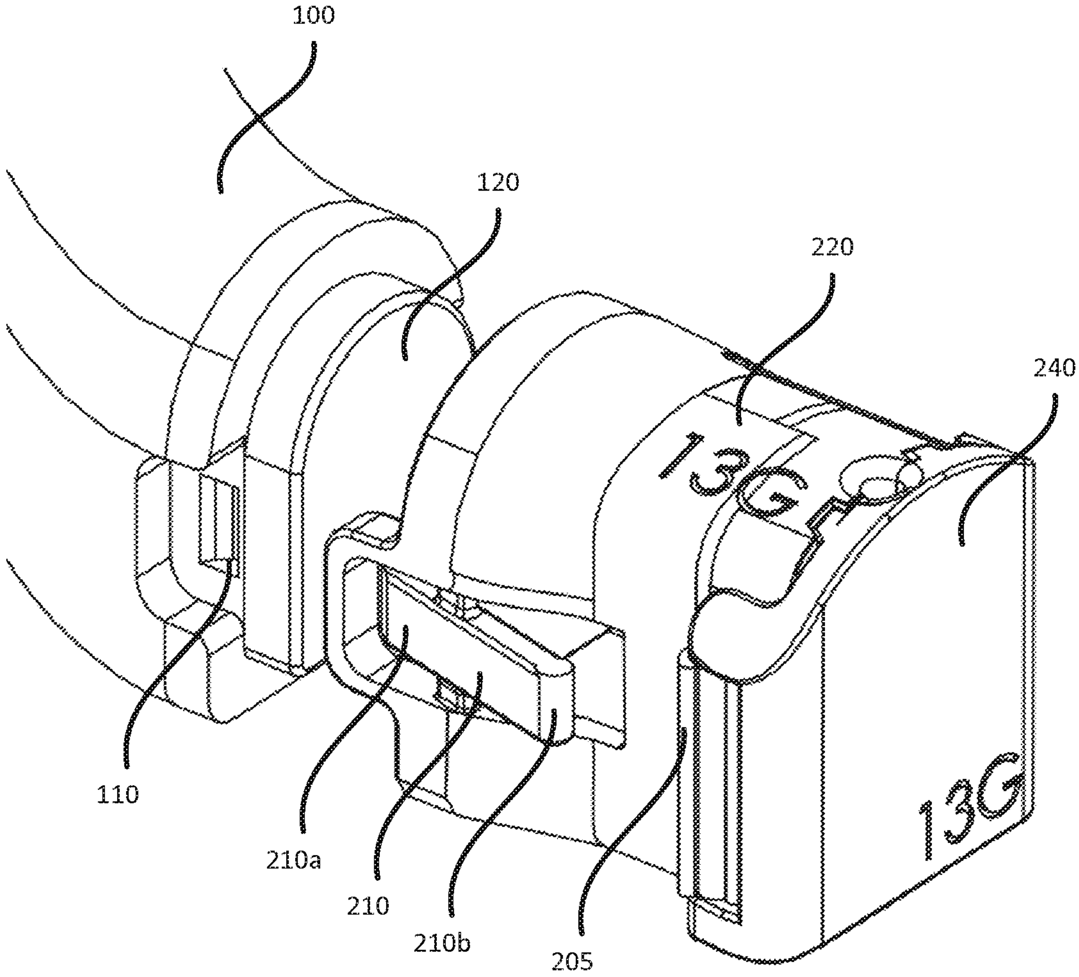
FIG. 5 shows a rendering of an end-effector with an exemplary end-effector attachment detached from the end-effector.

FIGS. 4-10 are renderings of end-effector attachments according to example embodiments of the invention. As shown in FIGS. 4 and 5, end-effector 100 and end-effector attachment 200 may each include mating structures shaped to be compatible with each other. In the example embodiment of these figures, the mating structures are dome-shaped bump-out 120, which extends from the end-effector, and corresponding dome-shaped hollow 220, which extends into the main body of the end-effector attachment. The shapes of mating structures (such as, for example, the domed shapes of elements 120 and 220) may be chosen to restrict attachment to a single or limited number of orientations between end-effector attachment 200 and end-effector 100. This permits a reliable attachment to the end-effector and prevents a user from inadvertently attaching end-effector attachment 200 in an incorrect orientation, such as upside-down.

Configuration of an end-effector attachment with a torsional snap fitting and mating structures may improve the process of installing the end-effector attachment by permitting a user to easily and reliably perform attachment and detachment. In an example embodiment, the outer end 210*a* of torsional snap fitting 210 may be extended away from the main body of end-effector attachment 200 (by a user pressing on the inner end 210*b* of the torsional snap fitting, for example) during the mating of the end-effector attachment to end-effector 100 and then subsequently retracted (by releasing the inner end, for example) to lock into groove 110, thereby providing a secure attachment of the end-effector attachment 200 to the end-effector 100. Once attached, end-effector attachment 200 may be detached (again by pressing on the extended inner end) to unlock snap fitting 210 to from the mated groove 110. Thus, the torsional snap fitting 210 secures the end-effector attachment 200 steadily with the end-effector 100 during operation of the robotic guide system. The torsional snap fitting 210 also allows a user to attach and detach end-effector attachment 200 using a single hand, permitting the rapid release of the end-effector attachment 200 from the end-effector 100, as may be desired or necessary when an emergency occurs during operation.

FIG. 5 also shows an example configuration of attachment between the main body of the end-effector attachment and the pivotable door that permits the pivotable door to pivot between open and closed positions. In particular, the main body of end-effector attachment 200 includes fitting 205, into which an end of pivotable door 240 can be press fitted, thereby attaching it to main body 200. However, the configuration shown in FIG. 5 is merely exemplary, and other example embodiments may use a different configuration, such as a butt hinge design or lift-off hinge design.

Figure 6:
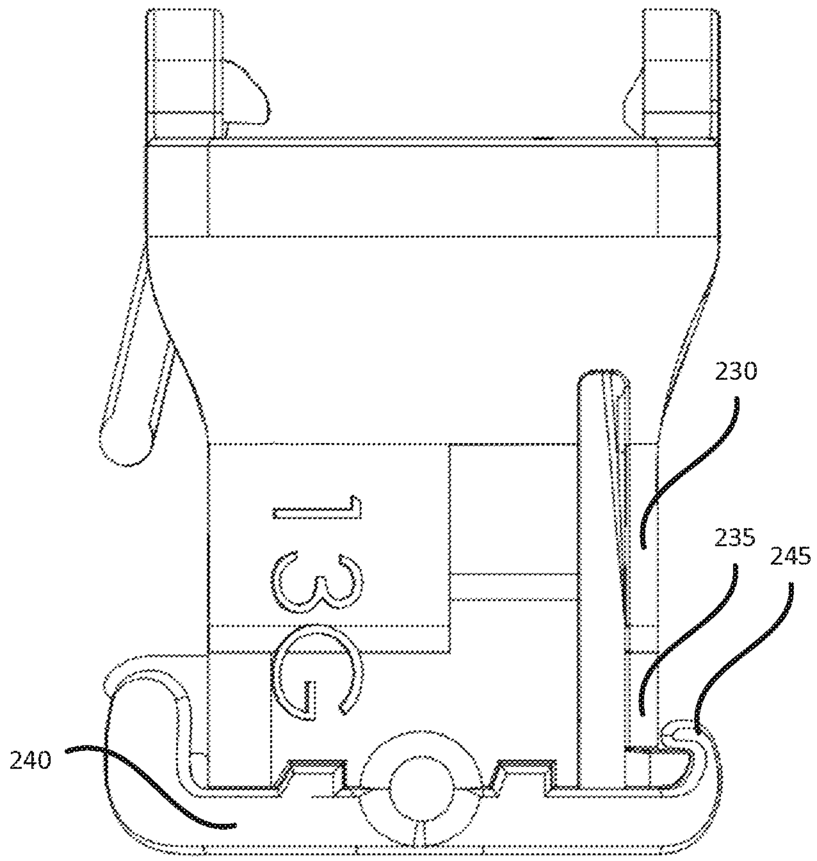
FIG. 6 shows a rendering of an exemplary end-effector attachment with a pivotable door in an open position.
Figure 7:
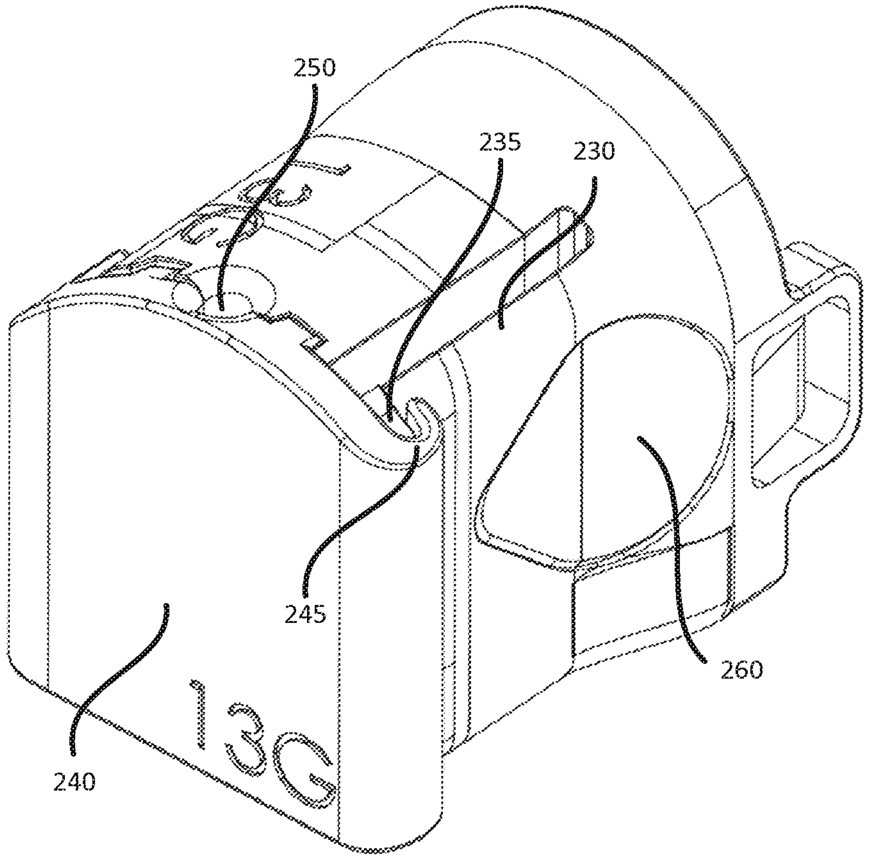
FIG. 7 shows a rendering of an exemplary end-effector attachment with a pivotable door in a closed position.
Figure 8:
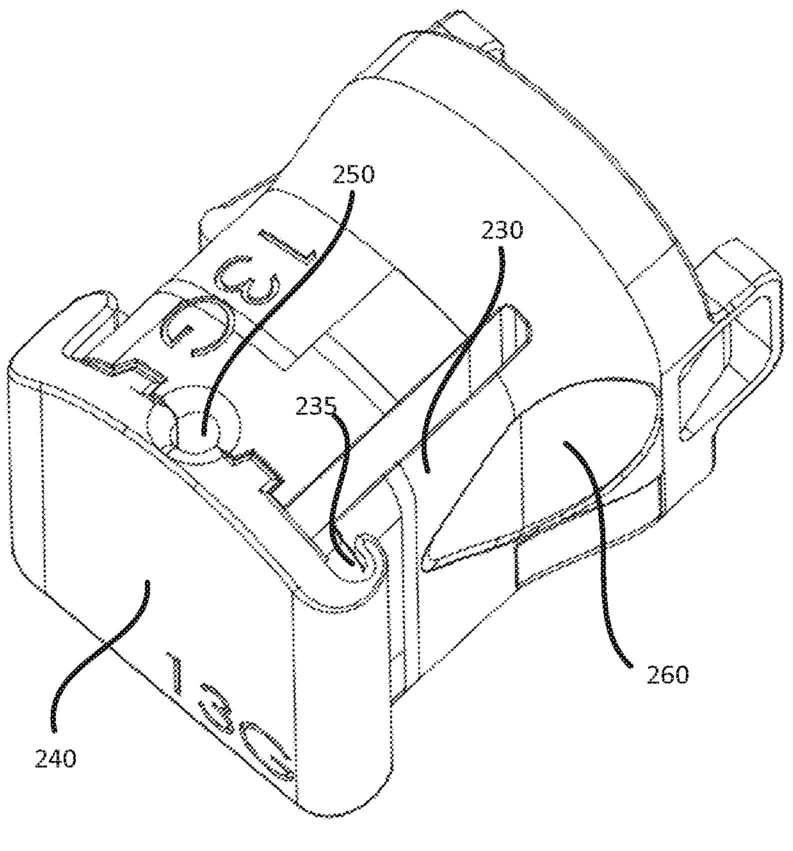
FIG. 8 shows a rendering of an exemplary end-effector attachment with a pivotable door in a closed position.

Features of the pivotable door 240 in example embodiments are further illustrated by FIGS. 6-8. As discussed above, flexible plate 230 is configured to act as locking mechanism for pivotable door 240. In example embodiments of the invention, this is achieved by configuring both the pivotable door and the flexible plate with hooked ends. Specifically, when the door is closed by a user, a hooked end 245 of the door presses against the hooked end 235 of the flexible plate 230, causing the plate to deflect due to the pushing force until the hooked end 245 of the door engages with the hooked end 235 of the plate, resulting in a snap fit between the door 240 and plate 230. This engagement is shown in FIG. 7. When it occurs, it can cause an audible clicking sound to indicate to the user that the pivotable door 240 is securely constrained.

To subsequently release the pivotable door, flexible plate 230 can be deflected (by a user pressing on it, for example), thereby unlocking the door 240 and allowing it to pivot freely. As shown in FIGS. 7 and 8, an imprint 260 may be included on flexible plate 230 to indicate to the user where to press to deflect the plate and unlock the pivotable door 240.

Figure 9:
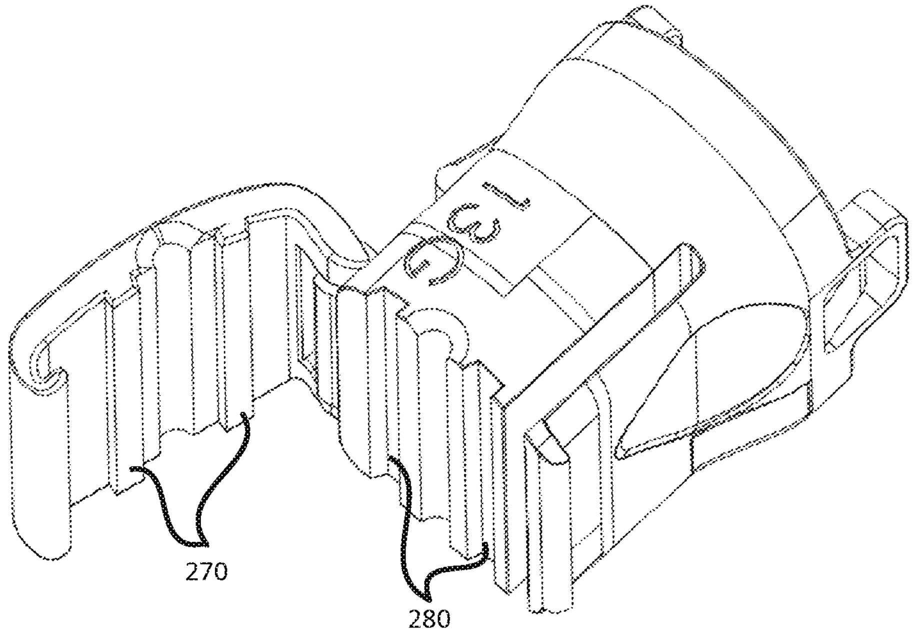
FIG. 9 shows a rendering of an exemplary end-effector attachment with a pivotable door in an open position.

In example embodiments of the invention in which end-effector attachment 200 is used to securely hold a needle, the circularity of entry point 250 may be further improved by the use of mating structures on the pivotable door 240 and flexible plate 230. FIG. 9 shows an example embodiment that incorporates this feature. Specifically, the end-effector attachment includes locating ribs 270 on the interior surface of pivotable door 240, as well as corresponding cut-outs 280 on the outer surface of the main body 200 of the end-effector attachment. When the pivotable door 240 is moved to a closed position, the ribs 270 mate with the cut-outs 280, thereby ensuring that the entry point 250 is a circular hole.

Those skilled in the art will recognize that the present teachings are amenable to a variety of modifications and/or enhancements. For example, although one or more example embodiments may have been described in the context of end-effector attachments usable to securely hold a needle, it should be understood that the invention is not so limited, and that in practice the example embodiments herein may be employed to securely hold other instruments. Accordingly, the specification is to be regarded as illustrative rather than restrictive, and modifications and changes may be made without departing from the broader spirit and scope of the specification.

While the foregoing has described what are considered to constitute the present teachings and/or other examples, it is understood that various modifications may be made thereto and that the subject matter disclosed herein may be implemented in various forms and examples, and that the teachings may be applied in numerous applications, only some of which have been described herein. It is intended by the following claims to claim any and all applications, modifications, and variations that fall within the true scope of the present teachings.

We claim:

1. An end-effector attachment for a robotic guide system comprising:
- a main body that includes an end configured to attach to an end-effector; and
- a pivotable portion attached to the main body, wherein the pivotable portion is configured to pivot between a closed position, in which a first surface of the pivotable portion contacts a first surface of the main body, and an open position, in which the first surface of the pivotable portion does not contact the first surface of the main body,
- wherein the first surface of the pivotable portion and the first surface of the main body are shaped to provide a cavity through the end-effector attachment.

2. The end-effector attachment according to claim 1,
- wherein the cavity is configured to hold an instrument guidable by the robotic guide system.

3. The end-effector attachment according to claim 2,
- wherein the instrument is a needle.

4. The end-effector attachment according to claim 1, further comprising:
- a flexible portion on the main body, wherein the flexible portion is configured to be deflected by a user,
- wherein in the closed position, the pivotable portion is engaged with the flexible portion such that the pivotable portion cannot pivot to the open position without deflection of the flexible portion, and
- wherein in the open position, the pivotable portion does not contact the flexible portion.

5. The end-effector attachment according to claim 4,
- a hinge portion on the main body,
- wherein the pivotable portion is attached to the main body at the hinge portion.

6. The end-effector attachment according to claim 5,
- wherein hinge portion is at an end of the main body opposite from the end configured to attach to an end-effector, and
- wherein the surface of the main body that contacts the pivotable portion is at the end of the main body having the hinge portion.

7. The end-effector attachment according to claim 6, further comprising:
- at least one mating portion on the surface of the main body that contacts the pivotable portion in the closed position; and
- at least one mating portion on the surface of the pivotable portion that contacts the main body in the closed position.

8. The end-effector attachment according to claim 7,
- wherein the at least one mating portion on the surface of the main body is a cut-out into the main body, and
- wherein the at least one mating portion on the surface of the pivotable portion is a rib extending from the pivotable portion.

9. The end-effector attachment according to claim 8,
- wherein the flexible portion is a plate extending from the main body in a direction from the end configured to attach to an end-effector to opposite end of the main body.

10. The end-effector attachment according to claim 9,
- wherein the end of the plate extending from the main body is hooked,
- wherein movement of the pivotable portion from the open position to the closed position requires the hooked end to deflect, and
- wherein in the closed position, the pivotable portion is prevented from pivoting to the open position by the hook.

11. An end-effector attachment for a robotic guide system comprising:
- a main body;
- a rotatable portion on an outer surface of the main body, wherein the rotatable portion has a first end configured to engage with an end-effector and a second end configured to be actuated by a user, wherein rotation of the rotatable portion causes the first end of the rotatable portion to move away from the main body and the second end of the rotatable portion to move towards the main body; and
- a cavity that extends through the main body, wherein the cavity is configured to hold an instrument guidable by the robotic guide system.

12. The end-effector attachment according to claim 11,
- wherein the instrument is a needle.

13. The end-effector attachment according to claim 11,
- wherein the first end of the rotatable portion is shaped to mate with a cut-out portion on the end-effector.

14. The end-effector attachment according to claim 13, further comprising:
- a mating portion on the main body configured to mate with a mating portion on the end-effector.

15. The end-effector attachment according to claim 14,
- wherein the mating portion on the main body is a hollow portion extending into the main body.

16. A method for using an end-effector attachment comprising:
- providing an end-effector attachment that includes
- (i) a main body,
- (ii) a rotatable portion on an outer surface of the main body,
- (iii) a mating portion on the main body configured to mate with a mating portion on an end-effector,
- (iv) a pivotable portion attached to the main body, wherein the pivotable portion is configured to pivot between a closed position, in which a first surface of the pivotable portion contacts a first surface of the main body and causes a cavity to be formed in the end-effector attachment, and an open position, in which the first surface of the pivotable portion does not contact the first surface of the main body;

(v) a flexible portion on the main body, wherein in the closed position, the pivotable portion is engaged with the flexible portion such that the pivotable portion cannot pivot to the open position without deflection of the flexible portion;

actuating the rotatable portion to cause a first end of the rotatable portion to move away from the main body and a second end of the rotatable portion to move towards the main body, wherein the first end is configured to engage with a cut-out portion of the end-effector and the second end is configured to be actuated by a user;

mating the mating portion of the end-effector attachment with the mating portion of the end-effector; and actuating the rotatable portion to cause the first end of the rotatable portion to engage with the cut-out portion on the end-effector.

17. The method of claim 16, further comprising:

positioning an instrument where the cavity in the end-effector attachment can be formed by contact between the first surface of the pivotable portion and the first surface of the main body; and pivoting the pivotable portion from the open position to the closed position.

* * * * *